US008757189B2

(12) United States Patent
Cooksey (10) Patent No.: US 8,757,189 B2
(45) Date of Patent: Jun. 24, 2014

(54) FLUID DELIVERY SYSTEM (75) Inventor: Gregory A. Cooksey, Gaithersburg, MD (US)

(73) Assignees: The United States of America, as Represented by the Secretary of Commerce, Washington, DC (US); The National Institute of Standards and Technology, Gaithersburg, MD (US)

( * ) Notice: Subject to any disclaimer, the term of this patent is extended or adjusted under 35 U.S.C. 154(b) by 583 days.

(21) Appl. No.: 12/912,300

(22) Filed: Oct. 26, 2010

(65) Prior Publication Data

US 2011/0180150 A1 Jul. 28, 2011

Related U.S. Application Data (60) Provisional application No. 61/298,575, filed on Jan. 27, 2010.

(51) Int. Cl.
*B08B 5/00* (2006.01)
*G01N 35/10* (2006.01)
*B01L 3/02* (2006.01)
*B01L 3/00* (2006.01)
*G05D 7/01* (2006.01)
*G01N 35/00* (2006.01)

(52) U.S. Cl.
CPC .......... *G05D 7/0193* (2013.01); *G01N 35/1072* (2013.01); *B01L 3/0293* (2013.01); *G01N 2035/1034* (2013.01); *B01L 2300/14* (2013.01); *B01L 3/50273* (2013.01); *G01N 2035/00158* (2013.01); *B01L 2400/0487* (2013.01); *B01L 3/502715* (2013.01)
USPC ........ 137/15.06; 137/142; 137/152; 137/206; 137/208

(58) Field of Classification Search
CPC ..... A01J 11/12; E04D 13/0404; B01D 23/28; B60K 15/077; B60K 15/00; B03D 1/14; B65D 90/00; B67D 1/0456; B67D 7/04; E03D 1/165; E03D 1/16; A01G 27/001; A61C 19/02; G01F 11/28; G01W 1/14; G05D 23/00; A01K 63/006; A01K 63/47; A01K 7/02; B67C 3/18; E03B 9/20; A23L 3/10; A61M 5/1689; A62C 13/003; B01J 4/001; B01J 19/0046
USPC .............. 137/135, 150.5, 146, 129, 131, 145, 137/208, 209, 206, 142, 152, 15.16
See application file for complete search history.

(56) References Cited

U.S. PATENT DOCUMENTS 1,668,419 A * 5/1928 Jefferson ....................... 137/152
2,078,384 A * 4/1937 Jefferson ....................... 137/267
2,363,177 A * 11/1944 Haffner ......................... 137/263
2,548,431 A * 4/1951 Hague ........................... 137/263

(Continued)

*Primary Examiner* — Craig Schneider
*Assistant Examiner* — Craig J Price
(74) *Attorney, Agent, or Firm* — Mark E. Bandy; Rankin, Hill & Clark LLP (57) ABSTRACT A fluid delivery system is described which provides stable flow rates over a range of different flow rates and while multiple fluids are being concurrently delivered. The delivery system includes one or more reservoirs each containing a respective fluid to be transferred. The reservoir(s) are positioned within a secondary fluid selected such that the reservoir(s) and their contents, i.e. the fluids to be transferred, float within the secondary fluid. One end of a flow conduit is submerged in each fluid to be transferred. A pressure differential is then induced in the flow conduit whereby fluid flow therein occurs.

27 Claims, 7 Drawing Sheets (56) References Cited

U.S. PATENT DOCUMENTS

| | | | |
|---|---|---|---|
| 2,947,316 A * | 8/1960 | Walker | 137/208 |
| 3,756,459 A | 9/1973 | Bannister et al. | |
| 4,666,430 A | 5/1987 | Brown et al. | |
| 5,678,591 A * | 10/1997 | Merrifield et al. | 137/208 |
| 5,857,589 A | 1/1999 | Cline et al. | |
| 6,532,983 B2 * | 3/2003 | Ganachaud | 137/264 |
| 7,220,593 B2 * | 5/2007 | Haubert et al. | 436/177 |
| 2005/0011582 A1 | 1/2005 | Haug | |
| 2006/0118167 A1 | 6/2006 | Neas et al. | |
| 2008/0245801 A1 | 10/2008 | Ullmann et al. | |

* cited by examiner

# FLUID DELIVERY SYSTEM

CROSS REFERENCES TO RELATED APPLICATIONS

This application claims priority upon U.S. provisional application Ser. No. 61/298,575 filed Jan. 27, 2010.

FIELD OF THE INVENTION

The present invention relates to systems and techniques for transferring one or more fluids to a desired location while performing such transfer with a relatively constant flow rate.

BACKGROUND OF THE INVENTION

Microfluidic devices are increasingly being utilized for complex chemical and biological applications, which can require connecting many different reagents, solvents, or buffers to a device. Current methods to deliver fluids to microdevices are in many cases not suitable for controlling large numbers of fluids or for maintaining constant flow rates over large delivered volumes. For example, syringe pumps are expensive, bulky, and prone to oscillations at low flow rates; integrated reservoirs have limited volume, must be incorporated into every device, and experience changes in flow rate as reservoirs drain; and horizontal reservoirs have limited fluid capacity and flow rates. Accordingly, a need exists for a new strategy and system for delivering one or more fluids to a target destination with greater controllability and stable flow rates as compared to currently known techniques and systems.

SUMMARY OF THE INVENTION

The difficulties and drawbacks associated with previously known systems are addressed in the present method and apparatus for a fluid delivery system.

In one aspect, the present invention provides a fluid delivery system comprising a rigid walled reservoir containing a first fluid to be transferred from the reservoir. The system also comprises a flow conduit having an inlet end disposed in the reservoir and submerged in the first fluid. And, the system comprises a container including a second fluid. The reservoir containing the first fluid is floating in the second fluid.

In another aspect, the invention provides a fluid delivery system comprising a container defining an interior region and a flotation fluid disposed within the interior region. The fluid delivery system also comprises at least one reservoir containing a fluid to be delivered. At least one reservoir and fluid to be delivered is floating within the flotation fluid. The system additionally comprises flow conduit(s) having inlet end(s) disposed in the reservoir(s) and submerged in the fluid(s) to be delivered. And, the fluid delivery system comprises support provisions disposed within the container and defining a support region within which is disposed at least one reservoir, wherein the support provisions maintain the reservoir(s) in consistent orientation during delivery of the fluid.

In yet another aspect, the invention provides a method for transferring a fluid from a reservoir. The method comprises providing a reservoir containing a first fluid to be transferred. The method also comprises providing a container including a second fluid. The method additionally comprises providing a flow conduit defining an inlet end and an opposite outlet end. The method further comprises submerging the inlet end of the flow conduit in the first fluid contained in the reservoir. And, the method comprises floating the reservoir containing the first fluid in the second fluid. Upon establishing a sufficient pressure differential across the inlet and outlet ends of the flow conduit, flow of the first fluid within the conduit is induced.

As will be realized, the invention is capable of other and different embodiments and its several details are capable of modifications in various respects, all without departing from the invention. Accordingly, the drawings and description are to be regarded as illustrative and not restrictive.

BRIEF DESCRIPTION OF THE DRAWINGS

FIG. 5 also includes a detailed photograph of a liquid junction in the microfluidic device.

DETAILED DESCRIPTION OF THE EMBODIMENTS

The present invention relates to systems and methods for administering one or more fluids in a controlled manner. Specifically, the invention provides for transfer of a fluid from a source reservoir to a destination location in which the fluid flow rate is very stable and variations in flow rate are significantly less as compared to known systems using conventional fluid transfer techniques.

In accordance with the invention, a reservoir or vial containing the fluid to be transferred is placed within a second fluid so that the reservoir and its fluid contents float on or within the second fluid. For applications in which multiple fluids are to be transferred, multiple reservoirs can be placed in the second fluid so that all the reservoirs are floating in the same secondary fluid. The reservoir(s) is preferably a rigid walled reservoir which maintains its shape and configuration independent of its contents. Such rigid walled reservoirs are in contrast to flexible wall pouches, bags or the like which could also contain one or more fluids. Flexible wall bags for example readily deform and change shape depending upon the amount and type of fluid contained within the bag. Accommodations would need to be made for flexible walled bags such that they could be easily organized within the container and remain separated from the secondary fluid. Although generally less preferred, the invention includes the use of reservoirs having flexible or deformable walls.

The secondary fluid is preferably retained within a container. The container may optionally include one or more support members that assist in maintaining a desired orientation of the reservoir(s) while floating within the secondary fluid. A wide array of container shapes, profiles, and configurations may be used. Wide containers will generally hold or accommodate a greater number of reservoirs, larger reservoirs, and/or wider reservoirs. Taller containers will enable taller reservoirs to be used.

Preferably, for a sealed container, the container height is about twice (or more) the height of the reservoir(s) retained within the container. This configuration enables a stationary inlet end of the flow conduit to remain submerged over the course of fluid dispensing. By providing a container with such height, ample clearance exists for the reservoir to be buoyed upward as the fluid in the reservoir is dispensed. It is also contemplated that the container height could be less than twice the height of the reservoir if for example the reservoir had flexible or deformable walls. Thus, as fluid is dispensed from the reservoir, the reservoir could rise and the walls of the reservoir would collapse or move away from a top member or lid of the container to thereby avoid interfering with the upward displacement of the reservoir.

The reservoir may exhibit a wide array of shapes, profiles, and configurations. For example, the reservoir may have a cylindrical configuration which provides the smallest perimeter per surface area ratio of all reservoir shapes. This ratio determines the weight of the fluid per weight of the reservoir, which as described herein is a key parameter of achieving stable flow rates. Cylindrical shapes may also be preferred due to ease of holding for transportation or portability. Cylindrical shapes may also provide the highest packing density of reservoirs. Wider reservoirs will generally be more stable. Taller reservoirs will enable larger liquid volumes to be dispensed. Reservoirs having straight vertical sided configurations, e.g. cylindrical or rectangular shapes, are preferred as they are the easiest to constrain with support members. Additional shapes and/or configurations might also be useful such as cones, pyramids, bowls, and hyperboloids, as they may be used to change the response of the system as the reservoir drains, i.e. a cone or bowl having an upper narrow region would exhibit decreasing (rather than constant) changes in flow rate as it drained. And a similar shape but one in which the narrow region is located at a lower location would exhibit increasing deviations in flow rate during draining. The reservoirs may be open to the atmosphere, or may have interiors sealed off from atmospheric pressure. The reservoirs may include provisions for administering one or more gases within the reservoir interior such as to provide an elevated pressure within the interior.

A flow conduit such as a flexible tube, needle, hose, pipe, capillary tube, etc. is placed within each reservoir of interest such that an inlet end of the conduit is immersed in the fluid to be transferred. Flow of the fluid within the conduit occurs continuously after establishing a sufficient pressure differential across the inlet end and an outlet end of the conduit. Specifically, the inlet pressure is determined by the density of the fluid and the total height of the fluid in the reservoir above the outlet end (irrespective of the depth of the inlet end) in addition to any pressure applied to the fluid in the reservoir. Such pressure at the inlet end could be negative to draw fluid into the reservoir. Or, the pressure at the inlet end could be positive to force fluid out from the reservoir through the conduit. The outlet end of the flow conduit could also be pressurized in a positive or negative fashion. As noted, flow within the conduit occurs as a result of establishing a sufficient pressure differential across the conduit ends. The flow conduits may be provided in a range of different shapes, sizes, and styles. A preferred cross sectional shape is circular. The flow conduits could also have other shapes as desired to control their surface-to-fluid contact area.

Preferably, the inlet end of the flow conduit is stationary. However, the invention includes systems in which the inlet end moves or is movable. So long as the inlet remains submerged in the fluid being dispensed, it is not critical whether the inlet is stationary or moves.

The invention is based at least in part, upon a discovery that changes in hydrostatic pressure in the fluid being transferred occur as a result of draining of the reservoir, can be significantly reduced by floating the reservoir containing the fluid being transferred in a secondary fluid. Reduction of such hydrostatic pressure changes results in more stable and uniform flow rates of fluid from the reservoir. For example, for a gravity driven flow system in accordance with the invention, flows with 0.7% changes in flow rate per delivered ml have been demonstrated for a reservoir with approximately 110 $mm^2$ cross sectional area (1 ml/8.9 mm height). For an application with a flow rate of 1 microliter per minute, this results in flow rate changes of less than 1% (e.g. between 0.99 and 1 microliter per minute) for about 24 hours.

A useful metric for conveniently expressing the improved stability in flow rate of fluids delivered using the preferred embodiment systems described herein, is by reference to a system having the same components but in a nonfloating configuration. That is, comparison is made to a similar fluid delivery system having the same reservoir, flow conduit, and fluid being delivered at the same conditions, however the reservoir being positioned on a stationary surface or otherwise supported, and not floating in a flotation fluid. Thus, the term "reference system" as used herein refers to a similar fluid delivery system having the same reservoir, e.g. reservoir of the same size, shape, and mass, flow conduit, and fluid being delivered at the same conditions, however the reservoir being positioned on a stationary surface or otherwise supported, and not floating in a flotation fluid. The preferred embodiment fluid delivery systems exhibit at least a two fold improvement in flow stability as compared to a reference system that avoids floating the reservoir containing the fluid to be delivered. More preferably, the preferred systems exhibit at least a three fold improvement, more preferably a five fold improvement, more preferably a seven fold improvement, and most preferably a nine fold or more improvement in flow stability, as compared to a corresponding reference system. It is contemplated that the fluid delivery systems of the invention may deliver fluids with improvements in flow rate stability of more than ten fold as compared to corresponding reference systems.

As an example of the exceptional flow stability of the preferred embodiment fluid delivery systems, a drop in flow rate or deceleration as small as 0.0027 microliters/min$^2$/mm$^2$ was obtained using a preferred embodiment system with a floating reservoir of 11 mm inner diameter delivering flow at 250 microliters/min. When compared to a similar system however using a nonfloating reservoir, the system with the floating reservoir exhibited a deceleration, i.e. drop in flow rate, that was an improvement of approximately nine times better than the relatively large deceleration exhibited by the reference system—0.025 microliters/min$^2$/mm$^2$. Thus, in comparing the preferred embodiment system with a floating reservoir to a corresponding system with a nonfloating reservoir, the preferred embodiment system exhibited approximately a nine fold improvement in flow stability or flow uniformity. This feature of the preferred embodiment systems is referred to as an improvement in flow stability, i.e. exhibiting a smaller deceleration in flow as compared to a reference system.

The total weight of a reservoir during transfer of a fluid contained therein is the sum of the weight of the fluid and the weight of the reservoir. As fluid level within a reservoir decreases, the total weight of the reservoir is reduced. Reservoirs having different average densities (i.e. the empty reservoir mass divided by the enclosed volume) behave differently during fluid transfer from the reservoirs. Thus, in accordance with another preferred aspect of the invention, the weight of the reservoir is reduced for a given cross sectional area, which can be achieved using a lower density material or a by reducing the thickness of the walls of the material which define the reservoir. This results in the weight of the fluid constituting a larger proportion of the total weight of the reservoir plus the weight of the fluid during fluid transfer. Reducing the weight of the reservoir with a given cross-sectional area or increasing the cross sectional area of the reservoir with a given weight improves constancy of the fluid flow rate. These aspects are described in greater detail herein.

Additional control over flow rates can be achieved by sealing and pressurizing the container within which the one or more reservoirs are floating. For systems in which the one or more rigid walled reservoirs are open and not sealingly enclosed, establishing a desired pressure within the container also establishes the same pressure in the open interior(s) of the reservoir(s). Increasing pressure in the interior of the container reduces the impact that hydrostatic pressure has on the total pressure in the system. Thus, the flow rate is less dependent on the hydrostatic pressure as a reservoir drains. The preferred range of pressures used within the interior of the container is determined by the preferred range of flow rates and flow conduit diameters, i.e. flow rate is proportional to pressure/radius squared. Although not wishing to be bound to any particular values, generally, pressures within the interior of a sealed container of up to 20 psi (above atmospheric pressure) have been found useful. At 5 psi above atmospheric pressure, flow rates of approximately 1 ml/second with 1/16 inch inner diameter tubing are readily achievable. At 1 psi (above atmospheric pressure) within a sealed container, flow rates of 100 nl/minute or lower can be achieved at the outlet end of a flow conduit having a length of 400 inches or longer and an inner diameter of 0.01 inches or smaller. These aspects are described in greater detail herein.

Another technique for controlling fluid flow using the preferred embodiment systems is to select flow conduits having particular cross sectional fluid flow areas and/or internal surface characteristics to thereby adjust resistance to flow of fluid within the flow conduit. This and other aspects are all described herein in greater detail.

A unique fluid delivery system is provided that utilizes multiple floating fluid reservoirs to maintain stable hydraulic pressure at the outlet of a flow conduit even as the reservoirs drain. Many reservoirs can be positioned inside a small, sealed container, which facilitates portability and can maintain sterility. In addition, the entire set of fluids can be exchanged by switching the lid (with conduits attached) to an alternate container with different or refilled fluids. If the container is not sealed, reservoirs can be refilled at any time. Flow rates during refilling will only change (by only the very small amount that they may have changed due to hydrostatic pressure) back to the starting flow rates. Sealing the container also facilitates pressurization within the container, enabling higher flow rates and further improving stability. Because each reservoir floats independently inside the container, flow rates are balanced over large volumes and flow rates from different reservoirs remain similar even when the reservoirs are drained at different rates. Sealing the container also helps to maintain the volumes of volatile liquids or liquids which produce hazardous fumes.

Each fluid reservoir can float in a single container and so flows from each depend on balance of the whole system. Alternatively, a container with multiple independent compartments can be used so flows from each reservoir then balance independently. In the case of containers with multiple compartments, each compartment could have a different flotation fluid as well as a different height thereby enabling variations of density, pressure, and stability upon draining.

As described in greater detail herein, the systems may also include one or more support members for holding or otherwise retaining the floating reservoirs in a desired upright orientation. Preferably, the support member is shaped according to the interior configuration of the container that holds the flotation fluid. The support member generally defines an aperture within which a reservoir is located while floating in the flotation fluid. Support provisions are preferably positioned within the interior of the container and define one or more regions within which the reservoirs float. These regions serve to maintain the reservoir(s) in a desired orientation during delivery of fluid in the reservoir. Typically, a desired orientation is that a reservoir not tip or physically interfere with other reservoirs in the container. Thus, this is referred to herein as the reservoir being maintained in a consistent orientation during fluid delivery.

Various references are made herein regarding one or more vials or reservoirs positioned within another container having a secondary fluid such that the vials or reservoirs "float" within the secondary fluid. The secondary fluid is periodically referred to herein as the flotation fluid. The term "float" refers to the reservoir(s) containing the fluid(s) to be transferred being buoyant within the secondary fluid. During transfer of liquid from a floating reservoir, the weight of the reservoir and fluid in the reservoir is entirely supported by the secondary fluid, unless a damping system is placed to provide additional compensation for change in height of fluid inside the reservoir with respect to the outlet end of the conduit during draining of the fluid in the reservoir. That is, the weight of the reservoir and fluid therein is equal to the weight of the secondary fluid displaced by the reservoir (excluding damping compensation).

The present invention can be used to deliver a wide array of fluids at controlled and stable flow rates. The fluids may be nearly any material which flows at the conditions of the delivery, e.g. the pressure and temperature are such that the material is in a flowable state. The fluids can include liquids, gases and combinations of (i) liquids and gases and/or (ii) liquids and solids (e.g. suspensions or colloids). It is also contemplated that in certain applications, it may be possible to deliver a system of solids dispersed in a gas. For example, finely divided particulates could be suspended or otherwise entrained within a gaseous medium. Typical fluids include fluids used in microfluidic applications and large scale applications, including but not limited to water which may include any number of dissolved compounds of interest such as antibodies, antigens, enzymes, fluorescent dyes or substrates, nucleic acids, e.g. DNA and RNA etc.; cell culture media including but not limited to serum, proteins and enzymes, salts, sugars, etc.; salts and buffer solutions; alcohols; organics, e.g. hexanes; lipids or surfactants; nanoparticles; microbeads; and weak acids or bases. Large-scale applications might also include paints, oils, industrial reagents, etc.

The liquids suitable for transfer by the present invention can also be characterized by their viscosity. Generally, any liquid having a viscosity at the conditions of transfer of from about 0.1 cP to about 75,000 cP, can be transferred using the systems and strategies described herein. Preferably, the liquid(s) to be transferred have a viscosity of from about 0.3 cP to about 50,000 cP. Typical liquids that could be transferred include but are not limited to acetone having a viscosity of about 0.3 cP, water (0.9 cP), corn syrup (1400 cP), glycerol (1500 cP), and possibly ketchup (approximately 75000 cP, a non-newtonian fluid). Liquids with relatively high viscosities suffer from a disadvantage that their flow rate may be unacceptably slow. Low viscosities, in certain situations, can change the nature of the flow, such as from laminar to turbulent. Depending upon the particular application, relatively low viscosity may be undesirable.

The invention is fully compatible with suspensions, colloids, and emulsions. For example, it is contemplated that the preferred fluid delivery systems will find application particularly in the creation of suspensions, colloids, and emulsions such as in a liposome application described in greater detail herein.

Additional considerations for the preferred embodiment systems are as follows. In general, the density of the flotation fluid should be approximately equal to the density of the fluid to be delivered. It is also preferred that the flotation fluid be chemically compatible with the container and the reservoir floating in the flotation fluid. Surfactant or other additives may be added to the flotation fluid to reduce friction of the reservoirs against the walls of the container and/or an optional support member that holds the reservoirs in place inside the container.

Another variation of the present invention relates to the use of a damping system operably engaged between the reservoirs and the container such that the damping system cancels out the effect of the weight of the reservoirs or a portion thereof. Such damping systems may use a spring or other material that is selected and positioned to counter the force due to the mass of reservoir itself, which becomes a larger contributor of the total weight of reservoir and fluid therein as the reservoir empties. Preferably, the damping system includes one or more damping elements such as a dashpot which may be in the form of a hydraulic or mechanical damper, or a shock absorber which is configured to dissipate kinetic energy. Preferably, the damping system also includes one or more biasing elements such as springs. These aspects are described in greater detail herein.

The density of the flotation fluid could be dynamically varied over the course of a fluid delivery procedure. Removing or adding liquids, such as for fine tuning the behavior of the system is contemplated. Specifically, one or more liquids or soluble solids could be added to the secondary or flotation fluid to thereby change and preferably adjust the overall fluid density as desired, and likely to approximately match the density of the fluid(s) being transferred, particularly when the properties of the fluid are not well known.

Figure 1:
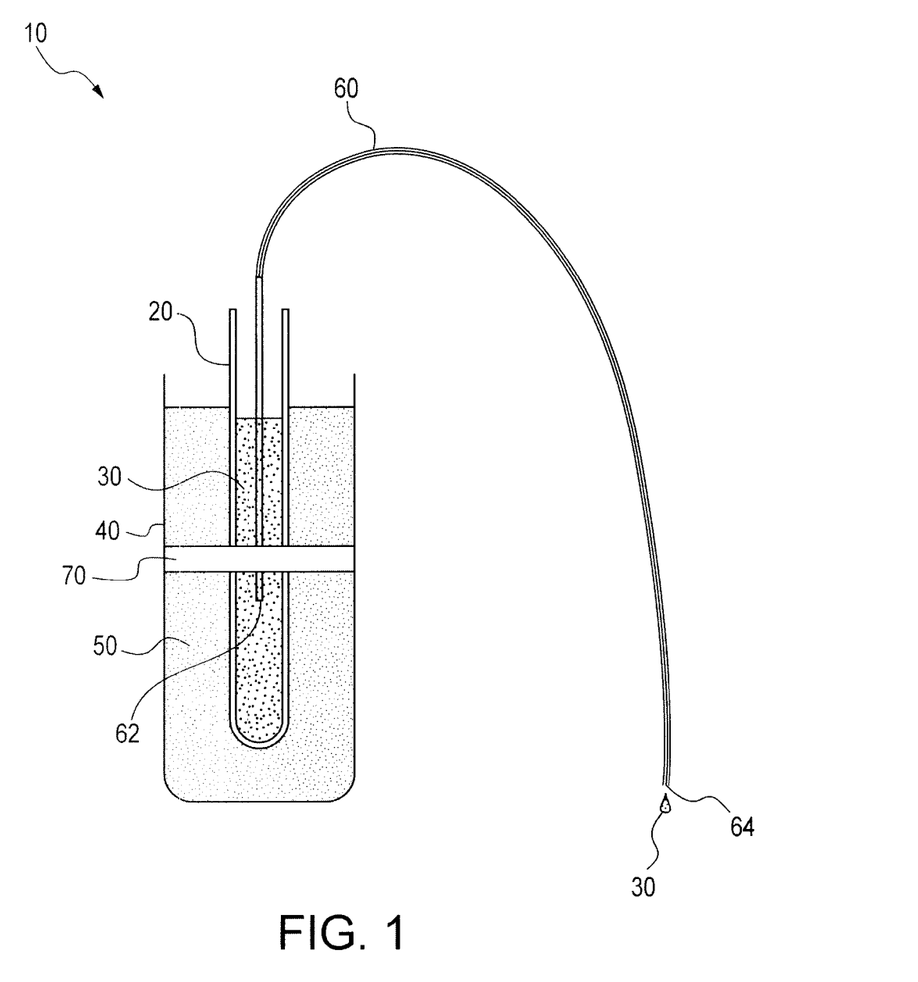
FIG. 1 is a schematic illustration of a preferred embodiment fluid delivery system in accordance with the present invention.

FIG. 1 schematically depicts a preferred embodiment fluid delivery system 10 in accordance with the present invention. The fluid delivery system 10 comprises a reservoir 20 containing a fluid 30 to be transferred, a secondary container 40 containing a flotation fluid 50, and a flow conduit 60. The fluids 30 and 50 may be the same or different. The reservoir 20 and its fluid 30 are positioned and floating within the flotation fluid 50. The flow conduit 60 defines an inlet end 62 and an outlet end 64. The flow conduit 60, and specifically its outlet end 64 is stationary. That is, during a fluid delivery operation, described in detail herein, the height or vertical position of the top of the fluid 30 relative to the height or vertical position of the outlet end 64 preferably does not change. The secondary container 40 optionally comprises one or more support members 70 to maintain a desired orientation of the reservoir. It will be appreciated that the support members 70 are configured such that they permit vertical displacement of one or more reservoirs such as reservoir 20 during a fluid transfer operation. Upon submersing the inlet end 62 of the flow conduit 60 within the fluid 30 to be transferred and establishing a sufficient pressure differential across the inlet and outlet ends 62 and 64, flow of the fluid 30 within the flow conduit 60 occurs whereby the fluid 30 is discharged at the outlet end 64 of the flow conduit 60.

Further details as to operation of the system 10 are as follows. As flow of fluid 30 occurs from the reservoir 20, through the inlet end 62, through the flow conduit 60, and exiting at the outlet end 64, the total height of the fluid 30 as measured from the bottom of the reservoir 20 decreases. The resulting decrease in weight of the reservoir contents, i.e. fluid 30, causes the reservoir 20 floating in the flotation fluid 50, to rise. The increase in vertical height of the reservoir 20 counteracts changes in hydrostatic pressure that would otherwise occur as the height of the fluid 30 relative to the reservoir 20 decreases. This strategy and system results in the flow rate of the fluid 30 as measured at the outlet end 64 of the flow conduit 60 to be very stable and exhibit minimal deviation.

Figure 2:
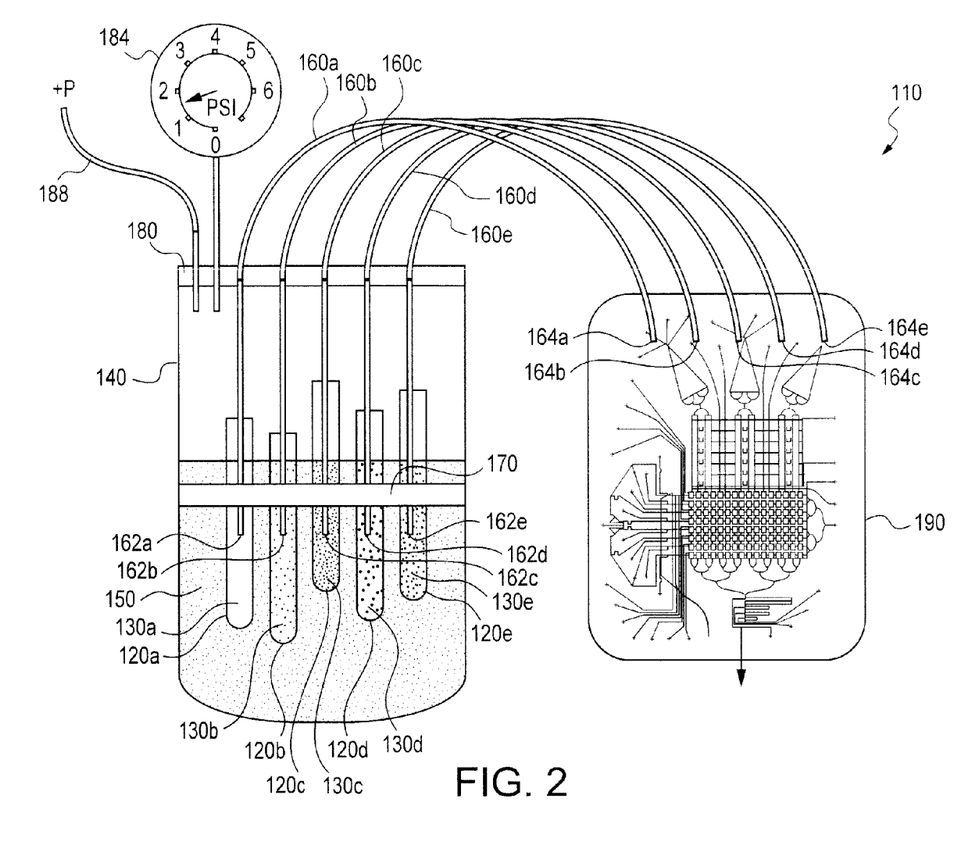
FIG. 2 is a schematic illustration of another preferred embodiment fluid delivery system in accordance with the present invention, providing a collection of different fluids to a microfluidic device.

In another aspect of the invention, a fluid delivery system is provided that comprises multiple, and in certain applications a large number of, floating fluid reservoirs in a pressurizeable container. This system addresses a long-standing problem of how to achieve stable flow rates in the μl/ml range from many fluid reservoirs simultaneously. FIG. 2 schematically illustrates a preferred embodiment fluid delivery system 110 in accordance with the present invention. The system 110 comprises a plurality of reservoirs 120 such as 120a, 120b, 120c, 120d, and 120e. Each reservoir contains a fluid 130 to be transferred, such as 130a, 130b, 130c, 130d, and 130e, respectively. The plurality of reservoirs 120 are positioned and floating within a flotation fluid 150 which resides within a secondary container 140. The container 140 preferably includes one or more support members 170 for retaining the reservoirs 120a-120e in a desired orientation. The fluids 130a-130e and 150 may be the same or different from one another. Associated with each reservoir and fluid to be transferred is a flow conduit 160 such as 160a, 160b, 160c, 160d, and 160e. Each flow conduit defines an inlet end and an opposite outlet end. Thus, conduit 160a includes inlet and outlet ends 162a and 164a. Conduit 160b includes inlet and outlet ends 162b and 164b. Conduit 160c includes inlet and outlet ends 162c and 164c. Conduit 160d includes inlet and outlet ends 162d and 164d. And, conduit 160e includes inlet and outlet ends 162e and 164e. The secondary container 140 includes provisions for selectively adjusting the pressure within the interior of the container. Preferably, the pressure adjusting provisions include a cover 180 sealingly affixed or engaged with the container 140, a pressure gauge 184 in communication with the interior of the container 140, and a pressure supply member 188 for establishing communication between the interior of the container 140 and a pressure source (not shown) such as a source of pressurized gas for example air, nitrogen, carbon dioxide, or helium. Generally, nearly any type of pressurized gas could be used and preferably an inert or non-reactive gas. However, it is also contemplated that the gas may be selected to react with or modify one or more parameters of the fluids to be dispensed. For example, for certain applications involving dispensing biological fluids, it may be preferred to include a minor proportion of carbon dioxide mixed with air or nitrogen to change the pH of the fluid. The particular choice of gas would correspond to the particular application and fluid(s) to be transferred. The pressure gauge 184 can be associated with a feedback control system in order to balance or control the pressure supply feeding into member 188.

The fluid delivery system 110 and specifically the outlet ends 164a-164e of the flow conduits 160a-160e, respectively, are in flow communication with a microfluidic device 190. It will be appreciated that in no way is the fluid delivery system 110 limited to applications with a microfluidic device. Instead, the fluid delivery system 110 can be used for providing one or more fluids at stable flow rates to nearly any device, location, or application.

Referring further to FIG. 2, a preferred operation of the fluid delivery system 110 is as follows. Upon establishing a sufficient pressure within the interior of the secondary container 140 such as by use of the pressure adjusting provisions, flow of the fluids 130a-130e is induced within the respective fluid flow conduits, 160a-160e. The fluids 130a-130e are discharged at the outlets 164a-164e, which thereby provide the fluids in a controlled manner and in stable flows to the microfluidic device 190.

As each of the fluids 130a-130e are transferred from their respective reservoir 120a-120e, respectively, the total weight of the respective fluids 130a-130e is reduced, thereby causing the reservoirs 120a-120e and their contents, i.e. the fluids 130a-130e, to rise relative to the outlet ends 164a-164e of the flow conduits 160a-160e. Increasing the total height of each reservoir counteracts the loss in hydrostatic pressure otherwise occurring as the fluid height decreases as fluid is transferred from the reservoir. As will be understood, this maintains the total height of each fluid relative to the outlet ends 164a-164e.

Figure 3:
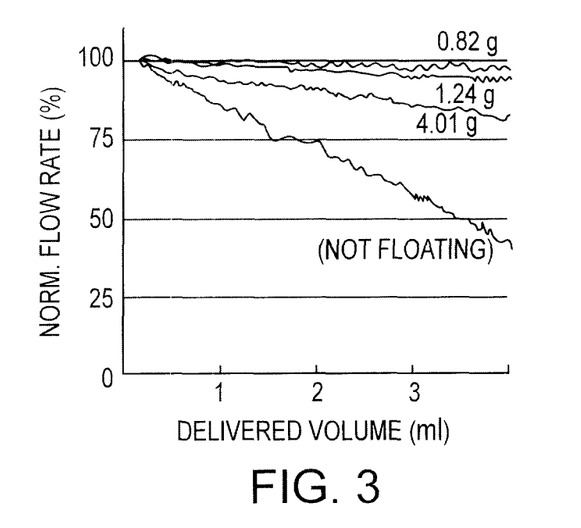
FIG. 3 is a graph of flow rates per delivered volume comparing several different reservoir types to transfer fluid using a preferred embodiment system as compared to a system that is not floating.
Figure 4:
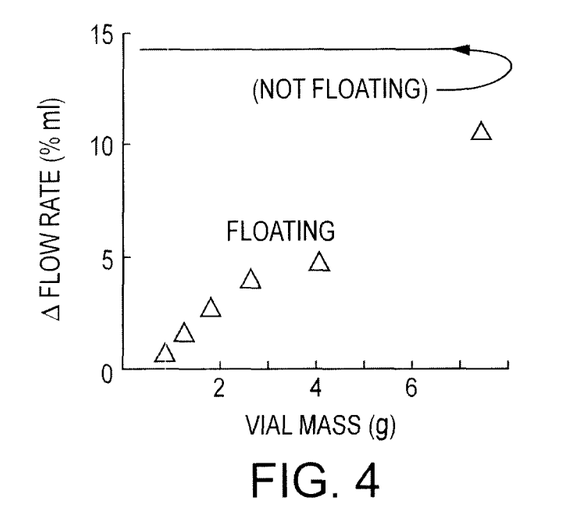
FIG. 4 is a graph of differences in flow rates per several reservoir masses using a preferred embodiment system as compared to a nonfloating system.

The performance of the preferred embodiment reservoir system shown in FIG. 1 was demonstrated by measuring fluid delivery from the single reservoir. Normalized flow rates and absolute changes in flow rate as a function of the delivered volume are shown in FIGS. 3 and 4, respectively. It has been observed that floating reservoirs within a secondary or flotation fluid considerably reduced changes in hydrostatic pressure as the reservoir drained, which greatly improved the stability of the flow rate over large delivered volumes. For example, flow rate from a 13 ml floating reservoir (0.82 g) decreased only 0.7% per ml of delivered fluid as compared to a 14% change per ml from a nonfloating reservoir, see FIG. 4. Much of the noise associated with the measurements in FIG. 4 are due to way in which the fluid mass was sampled at the outlet. Observation of the fluid flow in a microscope (e.g. FIG. 5) demonstrated smooth and uninterrupted flow.

Figure 5:
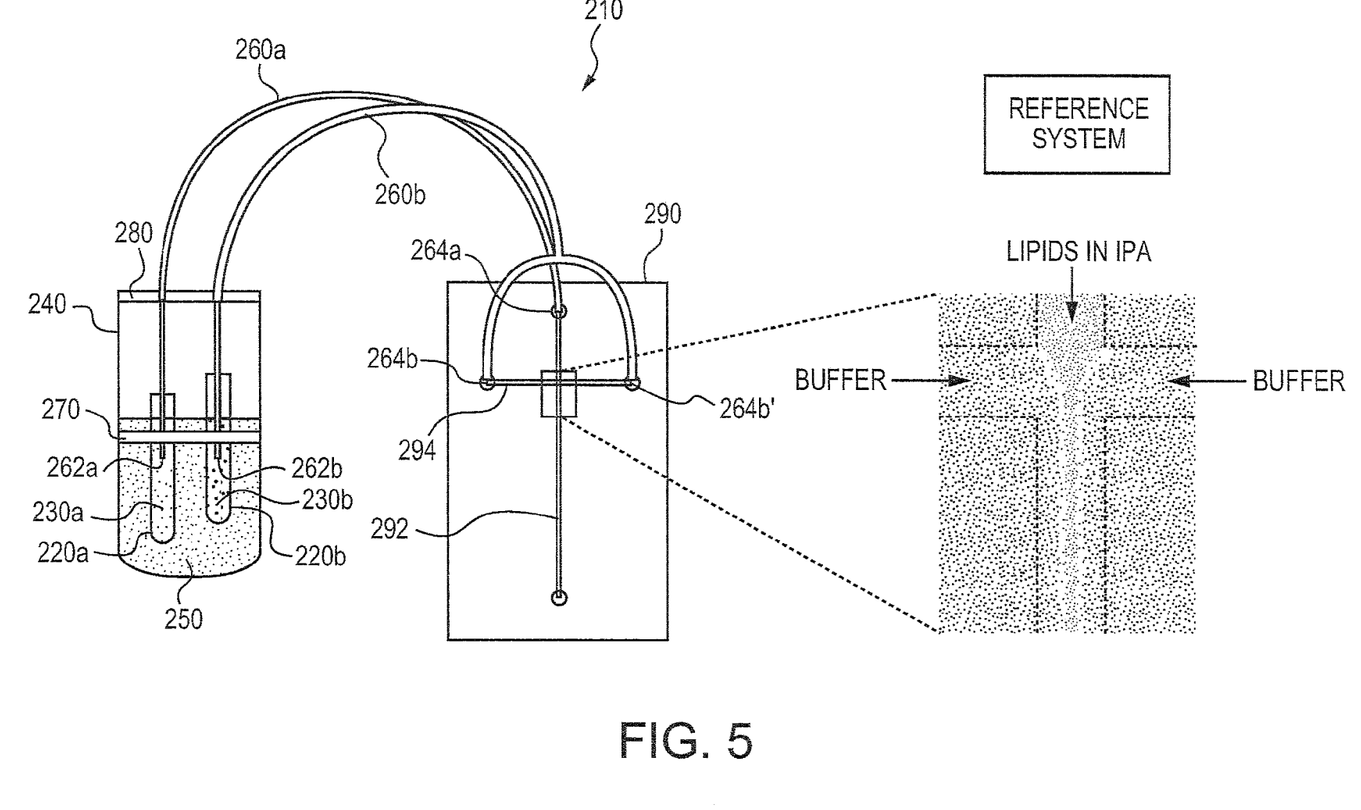
FIG. 5 is a schematic illustration of another preferred embodiment fluid delivery system in accordance with the invention, providing multiple fluids to another microfluidic device. This microfluidic device, for example, requires continuous and equal fluid flow rates in order to maintain constant chemical gradients in time.

FIG. 5 is a schematic illustration of another preferred embodiment fluid delivery system 210 in accordance with the invention. The system 210 comprises a container 240 and a flotation fluid 250 therein. The container 240 optionally includes a cover 280 to define a sealed interior within the container 240. Although not shown, it will be appreciated that the system 210 may further include a pressure gauge and/or pressurization provisions. Floating within the flotation fluid 250 are reservoirs 220a and 220b, containing fluids 230a and 230b, respectively, to be transferred. A flow conduit 260a is provided defining an inlet 262a which is submerged in the fluid 230a, and also defining an outlet 264a in communication with a microfluidic device 290. The microfluidic device 290 can be used in highly sensitive liposome formation procedures. A flow conduit 260b is also provided. The flow conduit 260b defines an inlet 262b submerged in the fluid 230b and, multiple outlets 264b and 264b' in communication with the microfluidic device 290. The container 240 includes one or more optional support members 270 to maintain a desired vertical orientation of each of the reservoirs floating within the fluid 250.

The microfluidic device 290 is interfaced with the fluid delivery system 210 such that the two outlets 264b and 264b' of the flow conduit 260b provide flow of the fluid 230b which may for example be a buffer solution to a pair of aligned channels 294 in the microfluidic device 290. The outlet 264a of the other flow conduit 260a is in communication with a transversely oriented channel 292 of the microfluidic device 290. A biological solution such as lipids dispersed in isopropyl alcohol (IPA) constitutes fluid 230a. As shown in FIG. 5, upon delivery of the fluids 230a and 230b, i.e. buffer and the biological solution, a controlled flow of lipids surrounded by a protective outer layer or sheath of buffer solution is provided which can then be further processed or reacted as desired. The ability to form highly controllable flow streams with extremely stable flow rates is demonstrated by the uniform appearance of the composite flow profile in FIG. 5. By use of the preferred fluid delivery systems described herein, the composite flow profile shown in FIG. 5 can be maintained over relatively long time periods, such as for example over the course of draining the contents of a reservoir containing a fluid of interest, or multiple reservoirs containing fluids of interest.

FIG. 5 also illustrates another aspect of the present invention in which flow rates and in particular ratios of flow rates of multiple fluids are controlled. Applications needing multiple fluids may require that the fluids be delivered at different rates or over different time intervals, which can lead to reservoirs emptying at different rates. Because hydrostatic pressure due to height of a fluid column can be a large contributor to fluid pressure, balancing the height of fluids as they drain is a useful and convenient strategy for maintaining constant flow rates. Different flow rates are necessary in applications such as the one illustrated in FIG. 5, in which a stream of one fluid of determined width is created within a stream of a second fluid of different width. Such different flow rates can be achieved, for example, by controlling the resistance of the flow conduits exiting the reservoir or internal to the specific application. Specifically, depending upon the flow cross sectional area and interior surface characteristics of each of the flow conduits 260a and 260b, particular ratios of fluid flows from the outlet ends of the conduits 260a and 260b can be achieved. For example, high resistance tubing or low resistance tubing or tubing of different diameters and lengths can be used for conduits 260a and 260b. For example, the application of FIG. 5 required a 25:1 flow rate ratio of lipids to buffer in order to generate nanoscale liposomes. These flow rates were realized by using a 70 inch length of 0.015 inch inner diameter tubing for lipids and a 15 inch length of 0.025 inch inner diameter tubing for the buffer. In other applications, systems were provided using 400 inch length tubing with 0.01 inch inner diameter and 5 inch length tubing with 0.0625 inch inner diameter. These values are not meant to determine limits of useful tubing sizes but merely to demonstrate regimes where such resistances have been found to be useful. Different fluidic volume demands from each reservoir can result from the specific needs of a particular microfluidic application, which could include, for example, accessing one fluid more frequently than other fluids using valving strategies that could be either internal or external to the given application or fluid delivery system 110.

Figure 6:
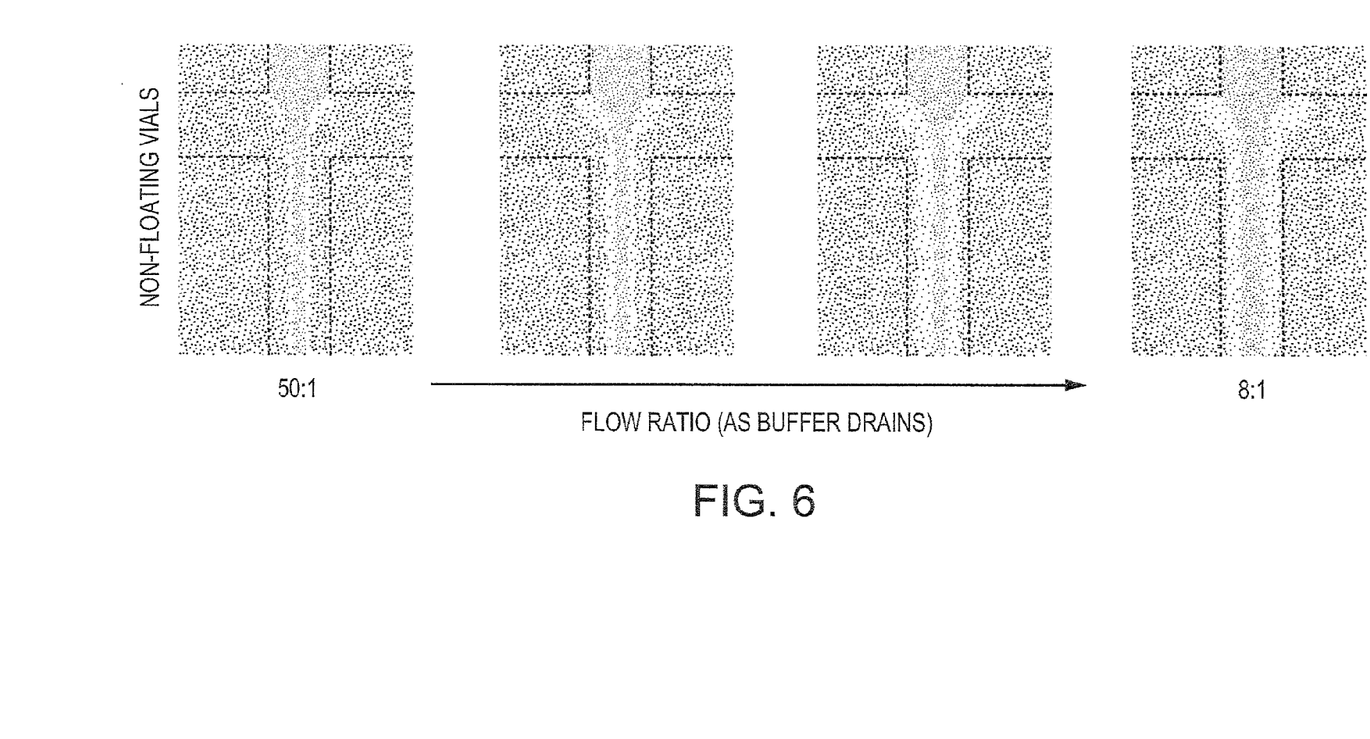
FIG. 6 includes several detailed photographs of liquid junctions in corresponding microfluidic devices like that of FIG. 5 using a nonfloating fluid delivery system, where fluid flow rates are not balanced with time.

FIG. 6 illustrates the same region of the microfluidic device 290 when the device receives a biological solution and a buffer from a conventional, nonfloating, hydrostatic reservoir system. The width of the fluid streams upon convergence in the central channel (dotted cross) is determined by the relative flow rates of the fluids, which was established by setting up a higher resistance conduit for the lipid solution (bright) compared to the buffer stream (dark). Because the tubing resistance of the buffer is much lower than the tubing resistance of the lipid solution, the buffer reservoir drains at a much faster rate, which, in a conventional nonfloating device, lowers the height of the buffer fluid compared to the lipid fluid. The reduced height of the buffer fluid results in slower flow rate compared to the lipid solution of the lipid solution, which widens the lipid stream. The changes in flows of the two fluids and particularly, the change in the ratio of the fluids over the course of draining of the reservoirs, cause significant disruption and eventual failure of the microfluidic device 290 to generate liposomes below a flow rate ratio of about 10:1. Specifically, FIG. 6 illustrates the changes in a composite flow profile as the ratio of fluids change over the course of reservoir draining in a conventional nonfloating reservoir system.

Figure 7:
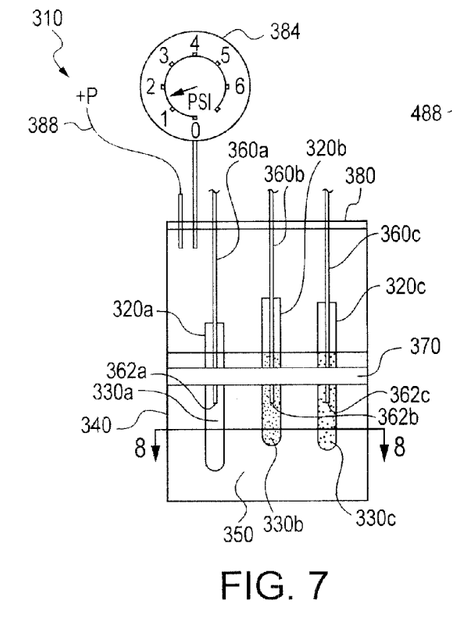
FIG. 7 is a schematic illustration of another preferred embodiment fluid delivery system in accordance with the present invention.
Figure 8:
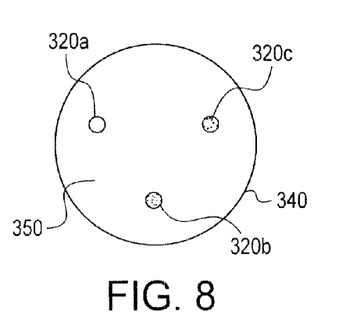
FIG. 8 is a schematic cross sectional view taken across line 8-8 in FIG. 7.

FIGS. 7 and 8 illustrate another preferred embodiment fluid delivery system 310. The system 310 comprises a secondary container 340 containing a flotation fluid 350. Floating within the fluid 350 are a plurality of reservoirs 320a-320c, containing fluids 330a-330c, respectively. Submerged in the fluids 330a-330c are inlets 362a-362c of flow conduits 360a-360c, respectively. A support member 370 having a plurality of apertures for receiving the reservoirs 320a-320c is provided. The system 310 may also comprise a cover 380, a pressure gauge 384, and a pressurization source 388. FIG. 8 is a schematic cross sectional view of the container 340 and its contents taken across line 8-8 in FIG. 7. FIG. 7 illustrates a system for delivering multiple fluids each having a different density, using a single flotation fluid.

Figure 9:
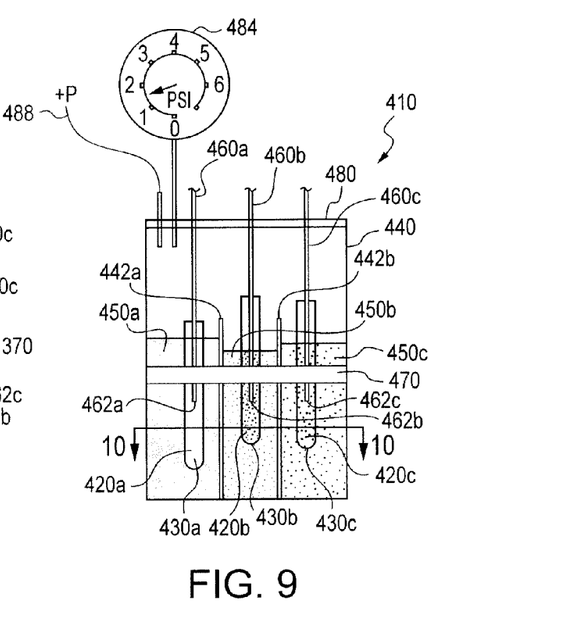
FIG. 9 is a schematic illustration of yet another preferred embodiment fluid delivery system in accordance with the present invention.
Figure 10:
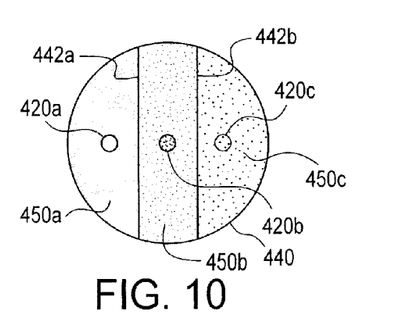
FIG. 10 is a schematic cross sectional view taken across line 10-10 in FIG. 9.

FIGS. 9 and 10 illustrate another preferred embodiment fluid delivery system 410. The system 410 comprises a secondary container 440 containing a plurality of flotation fluids 450a-450c. The fluids 450a-450c are segregated from one another by one or more partitions such as 442a and 442b. Floating within the fluids 450a-450c are a plurality of reservoirs 420a-420c, containing fluids 430a-430c, respectively. Submerged in the fluids 430a-430c are inlets 462a-462c of flow conduits 460a-460c, respectively. A support member 470 having a collection of apertures for receiving the reservoirs 420a-420c is provided. The system 410 may also comprise a cover 480, a pressure gauge 484, and a pressurization source 488. FIG. 10 is a schematic cross sectional view of the container 440 and its contents taken across line 10-10 in FIG. 9. FIG. 9 illustrates a system for delivering multiple fluids each having a different density, using multiple flotation fluids. Each flotation fluid may be selected or tailored such as by density adjustment to correspond to its respective fluid to be delivered.

Figure 11:
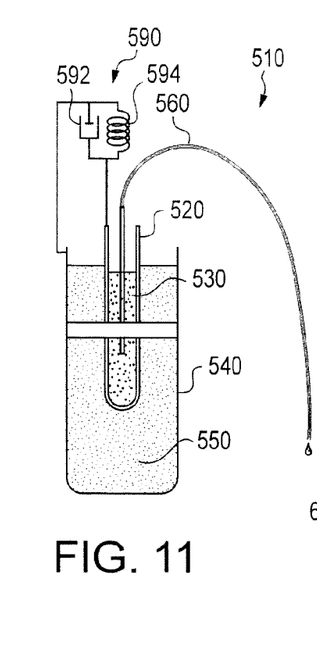
FIG. 11 is a schematic illustration of yet another preferred embodiment fluid delivery system including damping provisions in accordance with the invention.
Figure 12:
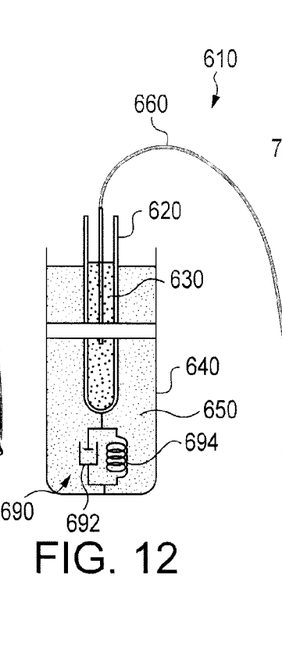
FIG. 12 is a schematic illustration of still another preferred embodiment fluid delivery system having damping provisions in accordance with the invention.
Figure 13:
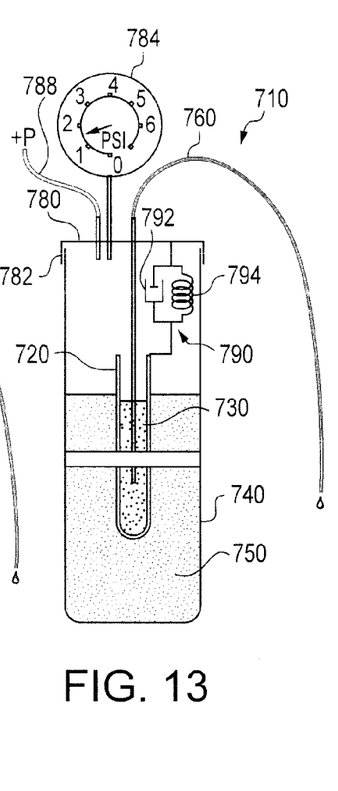
FIG. 13 is a schematic illustration of another preferred embodiment fluid delivery system having damping provisions in accordance with the present invention.
Figure 14:
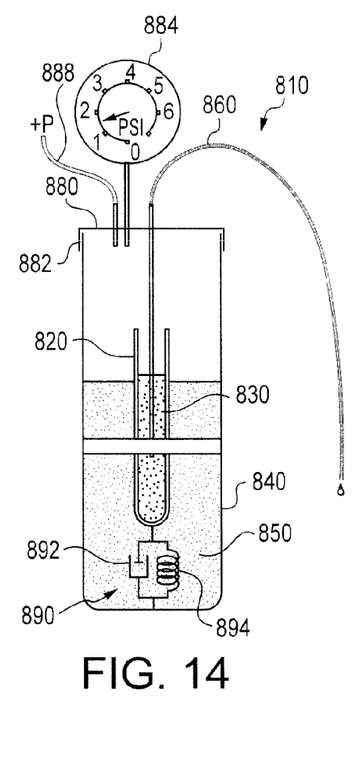
FIG. 14 is a schematic illustration of still another preferred embodiment fluid delivery system with damping provisions in accordance with the invention.

FIGS. 11-14 illustrate various preferred embodiment fluid delivery systems having damping provisions in accordance with the invention. The damping provisions are engaged or in communication with a reservoir and serve to reduce oscillation and/or reduce any undesirable effects otherwise occurring as a result of the weight of the reservoir during fluid delivery. FIG. 11 illustrates an open container where the volume of fluid in the container displaced by the reservoir and its fluid is greater than the volume of the fluid in the reservoir due to the mass of the reservoir. Restated, the density of the fluid in the container is nearly equal to or less than the density of fluid in the reservoir (considering the mass of the reservoir to be of minor consequence). In this case, the fluid in the reservoir is below the fluid level in the container and this level drops as fluid drains. The drop (leading to gradual reduction in hydrostatic pressure and slowing of fluid flow with draining) would be further reduced (in addition to floating) by the spring and/or damper system. FIG. 12 illustrates an open container where the volume of fluid in the container displaced by the reservoir and its fluid is smaller than the volume of the fluid in the reservoir (the higher density of the fluid in the container more than accounts for the mass of the reservoir). Restated, the density of fluid in the container is greater than the fluid density of fluid in the reservoir. In this case, the fluid in the reservoir is above the fluid level in the container and this level rises as fluid drains. The rise (leading to gradual increase in hydrostatic pressure and increase of fluid flow with draining) would be reduced by the spring and/or damper system. FIG. 13 illustrates a sealed container with an option for pressurization. In this embodiment, the fluid in the reservoir is floating below the level of the fluid in the container, as in the case illustrated in FIG. 11. Note that a seal is utilized between the lid of the container and the container. FIG. 14 shows a sealed container configured with the spring and/or damper on the bottom of the reservoir similar to the embodiment of FIG. 12.

Referring further to FIGS. 11-14, each of the preferred embodiment systems are described in greater detail as follows. The preferred embodiment fluid delivery system 510 depicted in FIG. 11 comprises one or more reservoirs 520 containing a fluid 530 to be delivered via a flow conduit 560. The system 510 also comprises a container 540 containing a flotation fluid 550. The reservoir 520 is floating in the flotation fluid 550. The preferred embodiment fluid delivery system 610 depicted in FIG. 12 includes similar components as described in association with FIG. 11, but identified via corresponding like numerals in the 600-series. Similarly, the preferred embodiment fluid delivery systems 710 and 810 depicted in FIGS. 13 and 14 respectively, include corresponding components having like reference numerals as the systems of FIGS. 11 and 12, but are in the 700 and 800-series, respectively. In addition, the preferred embodiment system 710 of FIG. 13 includes a pressure gauge 784 and a pressurization source 788. And, the system 810 of FIG. 14 includes a pressure gauge 884 and a pressurization source 888 as shown. In addition, each of the systems 710 and 810 include a cover 780 and 880, respectively, which is sealingly engaged to a corresponding container via a seal 782 and 882, respectively.

Each of the fluid delivery systems 510, 610, 710, and 810 includes damping provisions schematically depicted as 590, 690, 790, and 890, respectively. Each damping provision preferably includes a damping element, and a biasing element which is preferably in the form of a spring. Thus, damping provisions 590 include a damping element 592 and a biasing element 594. Likewise, the damping provision 610 of FIG. 12 includes a damping element 692 and a biasing element 694. The damping provision 710 of FIG. 13 comprises a damping element 792 and a biasing element 794. And the damping provision 810 of FIG. 14 includes a damping element 892 and a biasing element 894.

Preferably, in each damping provision, both of the damping element and the biasing element are in operable engagement with the reservoir. Thus, excessive displacement of the reservoir is reduced or countered as a result of the elements. The elements are preferably affixed or otherwise supported by the container or another stationary component such as for example a cover or lid, or a reservoir holder for example. It will be appreciated that the present invention includes the use of damping systems with one damping element or with one biasing element, or with multiples of each.

EXAMPLES

Example 1

A sealable container (Savillex Corp of Minnetonka, Minn.) was modified to hold multiple floating reservoirs. Polystyrene (4.01 g, Dow Corning), polyallomer (2.05 g, Becton Dickinson), and glass (7.5 g, Pyrex 9820, Cole Parmer) vials were used for the reservoirs. Reservoir mass was reduced by sanding. A multi-reservoir holder was made from poly(methylmethacrylate) (PMMA) to fit in the container. Holes matching the reservoir positions were drilled and tapped in the container lid to insert polypropylene (PP) end fittings, PP caps (Cole Parmer Instrument Co. of Vernon Hills, Ill., #R-06471 and #ZW-06471), and 16 gauge×101.6 mm needles (from Cadence, formerly Popper and Sons, Inc. of Lake Success, N.Y.). O-rings inserted between the end fittings and caps sealed around the needles. Holes for a pressurization inlet and pressure gauge were also made in the lid. Reservoirs filled within a few mm of their tops were loaded into the container, which was then filled with water to float the reservoirs. The lid was aligned to have needles over the appropriate reservoirs and screwed down to seal the container. Male luer hubs with one barbed end were used to connect the needles in the container lid to 0.635 mm inner diameter microbore tubing. Flow rates were determined by measuring the mass of water exiting the outlet over time. Flow rates were normalized to the initial rate, plotted against the volume delivered, and fit to a polynomial to determine the stability of the flow as a function of the reservoir mass. Poly(dimethylsiloxane) PDMS (Dow Corning) microfluidic devices and PMMA vacuum manifolds were made as previously reported (Cooksey G A, Plant A L, Atencia J. (2009) "A vacuum manifold for rapid world-to-chip connectivity of complex PDMS microdevices." *Lab on a Chip*, 9, 1298-300).

Example 2

A 19-reservoir system was prepared to demonstrate flow rate stability for a system with a large number of inlets. Replicate measurements from different reservoirs exhibited a mean flow rate of 30.2 µl/min and standard deviation of 1.34 µl/min. Over several different fluid pressures and fluidic resistances, the coefficient of variation was lower than 0.044 for replicates. These differences could perhaps be further reduced using more carefully matched tubing resistances, but it is noted that standard deviations of about 1 µl/min may be over estimated due to sampling error. The ability of the system, attached via a vacuum manifold, to deliver fluids to a complex microdevice was also demonstrated. Applications for fluid delivery systems having very stable and controllable flow rates are numerous. Furthermore, systems that can deliver multiple fluids concurrently are also expected to find wide use.

Preferred embodiment fluid delivery systems can transfer one or more fluids at exceedingly stable and uniform flow rates. For the specific reservoir and container dimensions used in one embodiment of the invention (example 1), flow change with time (e.g. flow deceleration) could be improved by 3-fold over a nonfloating system of the same dimensions using a 4 g reservoir of 140 mm cross sectional area with a capacity of 13 ml of fluid. More preferably, reducing the mass of the reservoir of the same diameter (2.6 g) resulted in a 5-fold improvement in flow stability with time compared to a nonfloating system. Most preferably, reducing the mass of the reservoir (0.8 g) resulted in a 9-fold improvement in flow stability with time. Although not wishing to be bound to any particular theory, it is believed that the stability of flow rate of a fluid delivered from the systems described herein is primarily a function of the following variables: (i) the weight of the reservoir with respect to the cross sectional area of inside the reservoir (reservoirs with lower average densities, e.g. empty weight divided by enclosed volume, would have increased flow stability), (ii) the height of the reservoir above the outlet of the flow conduit, and (iii) the pressure applied to the surface of the fluid in the reservoir being dispensed. Thus, it would be predicted that reducing the distance between the height of the fluid in the reservoir and the position of the outlet end of the reservoir or by lowering the cross sectional area for a given reservoir weight (e.g. increasing the average density of the reservoir) would produce an even greater disparity between floating and nonfloating systems (i.e. larger fold differences in flow rate stability with time).

The present invention systems and techniques do not require any external kinetic energy since they are all preferably gravity-driven. Furthermore, sophisticated and/or costly control systems are not necessary. Additional features and/or benefits which may be realized by the systems of the invention are as follows. The systems can be readily sterilized and are compatible for use with biological fluids. The systems, although not requiring any external power source, could be power assisted by a hand-held or manual pressurizing devices, such as a syringe. The systems are portable and thus can be easily transported. The systems can be quite small yet effective for 9 reservoirs in a single container each with stability of less than 1% change in flow rate per delivered ml and can be small enough to hold in one hand. The systems can also be configured to contain the fluids to be dispensed. And so, the systems do not release fumes or hazardous agents.

The various fluid delivery systems are particularly well suited for fluid delivery applications requiring precise control of flow rate and/or amount of fluid delivered over time. Although the preferred embodiment of the invention is to achieve a minimum rate of change of flow rate with time, the invention is also suitable for manipulation of the system parameters such that purposefully larger than zero changes in flow rate with time could be established. Furthermore, the fluid delivery systems can be readily adapted whereby the density or other properties of the flotation fluid can be readily adjusted. The ability of the fluid delivery systems to quickly and easily adjust and in certain applications to dynamically adjust flotation fluid properties during delivery of a target fluid, provides a significant advance in the art. Furthermore, the fluid delivery systems preferably include containers within which the flotation fluid resides, such that the container shields the flotation fluid from external conditions such as moving air streams or disturbances in the flotation fluid. This feature promotes a relatively quiet and static conditions in the flotation fluid during delivery of one or more target fluids.

It is also contemplated that the present invention can be utilized to provide fluid delivery systems that provide fluids at particular flow rates that vary in a predetermined fashion or more particularly, undergo a desired deceleration or acceleration in flow rate, i.e. change in flow rate over time. That is, by carefully selecting or designing the shape of a reservoir, changes in hydrostatic pressure in the fluid being transferred from the reservoir can be produced.

Many other benefits will no doubt become apparent from future application and development of this technology.

All patents, published applications, and articles noted herein are hereby incorporated by reference in their entirety.

It will be understood that any one or more feature or component of one embodiment described herein can be combined with one or more other features or components of another embodiment. Thus, the present invention includes any and all combinations of components or features of the embodiments described herein.

As described herein above, the present invention addresses many problems and deficiencies associated with previously known systems and practices. However, it will be appreciated that various changes in the details, materials and arrangements of parts, which have been herein described and illustrated in order to explain the nature of the invention, may be made by those skilled in the art without departing from the principle and scope of the invention, as expressed in the appended claims.

What is claimed is:

1. A fluid delivery system comprising:
    a reservoir containing a first fluid to be transferred from the reservoir;
    a flow conduit having an inlet end disposed in the reservoir and submerged in the first fluid; and
    a container including a second fluid;
    a support member affixed to the container, the support member defining an opening, wherein the reservoir is disposed within the opening while floating in the second fluid;
    wherein the reservoir containing the first fluid is floating in the second fluid such that a weight of the reservoir and the first fluid in the reservoir is entirely supported by the second fluid.

2. The fluid delivery system of claim 1 wherein the reservoir is a rigid walled reservoir.

3. The fluid delivery system of claim 1 wherein the reservoir is a flexible walled reservoir.

4. The fluid delivery system of claim 1 wherein the reservoir defines an unsealed interior in communication with atmospheric pressure.

5. The fluid delivery system of claim 1 wherein the first fluid in the reservoir and the second fluid in the container are both exposed to a common pressure.

6. The fluid delivery system of claim 5 wherein the first fluid in the reservoir and the second fluid in the container are exposed to atmospheric pressure.

7. The fluid delivery system of claim 5 wherein the common pressure is greater than atmospheric pressure.

8. The fluid delivery system of claim 1 wherein the reservoir is a first reservoir, the system further comprising:
    a second reservoir containing a third fluid to be transferred from the second reservoir,
    wherein the second reservoir containing the third fluid is also floating in the second fluid.

9. The fluid delivery system of claim 8 wherein the first fluid and the third fluid are different from one another.

10. The fluid delivery system of claim 1 wherein the first fluid and the second fluid are different from one another.

11. The fluid delivery system of claim 1 wherein the first fluid transferred from the reservoir through the flow conduit exhibits an improvement in flow stability of at least two fold as compared to a reference system using a nonfloating reservoir.

12. The fluid delivery system of claim 11 wherein the first fluid exhibits an improvement of at least five fold as compared to the reference system.

13. The fluid delivery system of claim 11 wherein the first fluid exhibits an improvement of at least ten fold as compared to the reference system.

14. The fluid delivery system of claim 1 wherein the container is sealed and includes provisions for selectively adjusting the pressure within the container.

15. The fluid delivery system of claim 8 wherein the container includes a partition for segregating the second fluid.

16. A fluid delivery system comprising:
    a container defining an interior region and a flotation fluid disposed within the interior region;
    at least one reservoir containing a fluid to be delivered, the at least one reservoir and fluid to be delivered floating within the flotation fluid;
    a flow conduit having an inlet end disposed in the reservoir and submerged in the fluid to be delivered; and
    support provisions disposed within the container and defining a support region within which is disposed in the at least one reservoir, wherein the support provisions maintain the reservoir in consistent orientation during delivery of the fluid and the weight of the at least one reservoir and the fluid to be delivered and contained in the at least one reservoir is entirely supported by the flotation fluid.

17. The fluid delivery system of claim 16 wherein the at least one reservoir includes a first reservoir containing a first fluid to be delivered, the fluid delivery system further comprising:
    a second reservoir containing a second fluid to be delivered;
    a flow conduit having an inlet end disposed in the second reservoir and submerged in the second fluid;
    wherein the second reservoir containing the second fluid is floating in the flotation fluid.

18. The fluid delivery system of claim 16 wherein the fluid to be delivered flows through the flow conduit at a relatively uniform flow rate and exhibits an improvement in flow stability of at least two fold as compared to a reference system using a nonfloating reservoir.

19. The fluid delivery system of claim 18 wherein the fluid to be delivered exhibits an improvement of at least five fold as compared to the reference system.

20. The fluid delivery system of claim 18 wherein the fluid to be delivered exhibits an improvement of at least ten fold as compared to the reference system.

21. The fluid delivery system of claim 16 wherein the container is sealed and includes provisions for selectively adjusting the pressure within the container.

22. A method for transferring a fluid from a reservoir, the method comprising:
   providing a reservoir containing a first fluid to be transferred;
   providing a container including a second fluid and support provisions disposed within the container, the support provisions defining a support region;
   providing a flow conduit defining an inlet end and an opposite outlet end;
   supporting the reservoir with the support provisions, wherein the support provisions maintain the reservoir in consistent orientation during delivery of the first fluid;
   submerging the inlet end of the flow conduit in the first fluid contained in the reservoir; and
   floating the reservoir containing the first fluid in the second fluid such that the weight of the reservoir and the first fluid in the reservoir is entirely supported by the second fluid.

23. The method of claim 22 further comprising:
   creating a pressure differential across the inlet end and the outlet end of the flow conduit to thereby induce transfer of the first fluid in the flow conduit.

24. The method of claim 23 wherein creating the pressure differential is performed by applying a pressure to the first fluid.

25. The method of claim 23 whereby the flow of fluid in the flow conduit represents an improvement of at least two fold as compared to a reference system using a nonfloating reservoir.

26. The methods of claim 23 whereby the flow of fluid represents an improvement of at least five fold as compared to the reference system.

27. The method of claim 25 whereby the flow of fluid represents an improvement of at least ten fold as compared to the reference system.

* * * * *